United States Patent [19]

Angelillo et al.

[11] Patent Number: 5,702,375

[45] Date of Patent: *Dec. 30, 1997

[54] ABSORBENT PAD AND THERMAL PACK

[75] Inventors: Stephen P. Angelillo, 2922 Cocovia Way, Leesburg, Fla. 32749; Richard E. Sweeting, Ocala, Fla.

[73] Assignee: Stephen P. Angelillo

[*] Notice: The term of this patent shall not extend beyond the expiration date of Pat. No. 5,178,139.

[21] Appl. No.: 493,527

[22] Filed: Jun. 22, 1995

Related U.S. Application Data

[63] Continuation of Ser. No. 254,490, Jun. 6, 1994, abandoned, which is a continuation of Ser. No. 78,867, Jun. 18, 1993, abandoned, which is a continuation of Ser. No. 822,887, Jan. 21, 1992, Pat. No. 5,277,180, which is a continuation of Ser. No. 487,856, Mar. 5, 1990, Pat. No. 5,178,139.

[51] Int. Cl.$^6$ .............................. A61F 13/15; A61F 7/00
[52] U.S. Cl. .............................. 604/358; 602/2; 604/387; 607/96; 607/108; 607/114
[58] Field of Search .............................. 602/1, 2, 900; 607/96, 104, 108, 114; 601/15; 604/291, 358, 387, 49

[56] References Cited

U.S. PATENT DOCUMENTS

| | | |
|---|---|---|
| Re. 32,026 | 11/1985 | Yamashita et al. . |
| 811,750 | 2/1906 | Spieske . |
| 1,384,747 | 7/1921 | Eckelmann et al. . |
| 1,385,074 | 7/1921 | Ferguson . |
| 1,434,576 | 11/1922 | Wertheimer . |
| 1,567,931 | 12/1925 | Epler . |
| 1,656,366 | 1/1928 | Sterling . |
| 1,819,807 | 8/1931 | Baysinger . |
| 1,901,313 | 3/1933 | Mann . |
| 1,910,874 | 5/1933 | Ziegler et al. . |
| 1,915,523 | 6/1933 | Ferguson . |
| 1,920,853 | 8/1933 | Ferguson . |
| 2,157,169 | 5/1939 | Foster . |
| 2,220,777 | 11/1940 | Othmer . |
| 2,289,425 | 7/1942 | Hogan . |
| 2,386,654 | 10/1945 | Caldwell . |
| 2,573,791 | 11/1951 | Howells . |
| 2,680,063 | 1/1954 | Shapiro . |
| 2,827,438 | 3/1958 | Bradley et al. . |
| 3,175,558 | 3/1965 | Caillouette et al. . |
| 3,223,081 | 12/1965 | Hunt . |
| 3,301,250 | 1/1967 | Glasser . |
| 3,475,239 | 10/1969 | Fearon et al. . |
| 3,585,982 | 6/1971 | Hollinshead . |
| 3,763,622 | 10/1973 | Stanley, Jr. . |
| 3,804,077 | 4/1974 | Williams . |
| 3,809,096 | 5/1974 | York ................................ 128/403 |
| 3,867,939 | 2/1975 | Moore et al. . |
| 3,874,504 | 4/1975 | Verakas . |
| 3,889,684 | 6/1975 | Lebold . |
| 3,905,367 | 9/1975 | Dapcich . |
| 3,950,158 | 4/1976 | Gossett ............................ 128/403 X |

(List continued on next page.)

FOREIGN PATENT DOCUMENTS

1383536  2/1975  United Kingdom .

*Primary Examiner*—John G. Weiss
*Assistant Examiner*—Dennis Ruhl
*Attorney, Agent, or Firm*—Frijouf, Rust & Pyle, P.A.

[57] ABSTRACT

An apparatus and method is disclosed for an improved absorbent pad and thermal pack for absorbing a liquid discharged from a patient. The absorbent pad and thermal pad comprises an outer sheet made of a liquid impermeable material and an inner sheet of a liquid permeable material. An absorbent sheet is disposed between the inner sheet and the outer sheet. A flexible liquid impermeable container having a chemical mixture which undergoes a thermal reaction upon activation thereof is interposed between the outer and inner sheets to enable the thermal source to be applied to the patient and to enable any liquid from the patient to permeate through the inner sheet to be absorbed by the absorbent sheet. The inner sheet of a liquid permeable material provides a moderate insulation barrier whereas the absorbent pad provides a substantial insulation barrier for directing the thermal source to the patient.

15 Claims, 4 Drawing Sheets

U.S. PATENT DOCUMENTS

| | | | |
|---|---|---|---|
| 3,976,049 | 8/1976 | Yamashita et al. | |
| 4,057,047 | 11/1977 | Gossett . | |
| 4,077,390 | 3/1978 | Stanley et al. | |
| 4,107,509 | 8/1978 | Scher et al. | |
| 4,142,508 | 3/1979 | Watson . | |
| 4,379,448 | 4/1983 | Kapralis et al. | |
| 4,397,315 | 8/1983 | Patel | 128/403 |
| 4,460,546 | 7/1984 | Kapralis et al. | |
| 4,462,224 | 7/1984 | Dunshee et al. | |
| 4,488,552 | 12/1984 | McCann et al. | |
| 4,532,110 | 7/1985 | Kapralis et al. | |
| 4,559,047 | 12/1985 | Kapralis et al. | |
| 4,580,547 | 4/1986 | Kapralis et al. | |
| 4,596,250 | 6/1986 | Belsang, III et al. | |
| 4,596,570 | 6/1986 | Jackson et al. | 604/387 |
| 4,756,311 | 7/1988 | Francis, Jr. | |
| 4,829,980 | 5/1989 | Smith . | |
| 4,834,739 | 5/1989 | Linker, III et al. | 604/386 X |
| 4,860,729 | 8/1989 | Benson et al. | |
| 4,872,442 | 10/1989 | Manker . | |
| 4,880,953 | 11/1989 | Manker . | |
| 4,899,727 | 2/1990 | Kapralis et al. | |
| 4,911,701 | 3/1990 | Mavinkurve | 604/385.2 |
| 5,056,589 | 10/1991 | Hettel et al. | |
| 5,058,563 | 10/1991 | Manker . | |
| 5,167,655 | 12/1992 | McCoy . | |
| 5,178,139 | 1/1993 | Angelillo et al. | 128/403 |
| 5,277,180 | 1/1994 | Angelillo et al. | 607/114 |
| 5,339,796 | 8/1994 | Manker . | |

ABSORBENT PAD AND THERMAL PACK

This application is a continuation of application Ser. No. 08/254,490 filed Jun. 6, 1994, now abandoned. Application Ser. No. 08/254,490 filed Jun. 6, 1994 is a continuation of application Ser. No. 08/078,867 filed Jun. 18, 1993 now abandoned. Application Ser. No. 08/078,867 filed Jun. 18, 1993 is a continuation of application Ser. No. 07/822,887 filed Jan. 21, 1992 now U.S. Pat. No. 5,277,180. Application Ser. No. 07/822,887 filed Jan. 21, 1992 is a continuation of application Ser. No. 07/487,856 filed Mar. 5, 1990 now U.S. Pat. No. 5,178,139.

BACKGROUND OF THE INVENTION

1. Field of the Invention

This invention relates to an improved absorbent pad and thermal pack for absorbing a liquid discharged from a patient and with improved insulation capabilities for the thermal pack.

2. Description of the Prior Art

The prior art has known various types of bandages, gauze and other types of absorbing material for absorbing blood and other fluids discharged from the body of the patient. These devices range in size and type from very large wraps of gauze material to small bandage type absorbent material with attached adhesive material for securing the absorbent material in a fixed position relative to the area of recovery of the patient.

A specific use of these types of absorbent bandages is in the area of obstetrics and gynecology. The prior art has known bandages which have been specifically contoured for comfortable positioning within the area of recovery of a obstetric or gynecological patient. Obstetric and gynecological bandages are formed to be generally rectangular with indentations or recesses on the opposed sides of the bandage midpoint between the opposed end having a general hourglass shape for a comfortable fit for the recovering obstetric or gynecological patient. Typically, the obstetric and gynecological bandages were worn within an undergarment which positioned and maintained the absorbent material proximate the recovering area of the patient.

Others in the prior art have utilized a thermal pack proximate a recovering area for cooling or heating the recovery area thus providing substantial relief from pain and discomfort for the patient. One type of thermal pack is formed from a flexible plastic container having a plurality of distinct chemical substances. Upon mixing of the chemical substances, a chemical reaction took place which underwent an endothermic or an exothermic reaction. Thermal packs which undergo an endothermic reaction are generally referred to as cold packs whereas thermal packs which undergo an exothermic reaction are generally referred to as hot packs. In a cold pack, heat is absorbed during the reaction of the two distinct chemical substances. Accordingly, the container and the chemical mixture within the container became cool relative to an ambient temperature thus absorbing heat from the recovering area to provide a cooling comfort and relief for the patient. The cold packs were generally positioned relative to the patient under a conventional bandage and were retained in place by an adhesive strip material or a strap device.

In a similar manner, a hot pack is formed from a flexible plastic container having a plurality of distinct chemical substances therein. Upon mixing of the chemical substances, a chemical reaction took place which underwent an exothermic reaction. The exothermic reaction produced heat during the reaction of the two distinct chemical substances. Accordingly, the container and the chemical mixture within the container became warm relative to an ambient temperature thus adding heat to the recovering area of the patient.

Unfortunately, in some cases the endothermic or exothermic reaction of the thermal pack made the thermal pack container too cold or too hot and uncomfortable for the patient. Furthermore, when a bandage was used simultaneously with the thermal pack, the thermal pack and the bandage became misaligned upon movement of the patient. In other cases, the thermal pack was retained in place by a resilient strap which was affixed about an extremity of the patient. However, the use of the resilient strap did not solve the problem of movement of the thermal pack relative to the absorbent pad.

Therefore, it is a primary object of the present invention to provide an improved absorbent pad and thermal pack with improved capabilities and which provides a significant advance in the bandage art.

Another object of this invention to provide an improved absorbent pad and thermal pack which eliminates the problems of alignment of the absorbent pad and the thermal pack on a recovering region of a patient.

Another object of this invention is to provide an improved absorbent pad and thermal pack which may be manufactured at a cost commensurate with a separate absorbent pad and a thermal pack.

Another object of this invention is to provide an improved absorbent pad and thermal pack which may be easily fitted and attached to a patient.

Another object of this invention is to provide an improved absorbent pad and thermal pack wherein the unit may be shipped as an integral unit.

Another object of this invention is to provide an improved absorbent pad and thermal pack which provides a moderate insulating layer interposed between the thermal pack and the skin of the patient for providing a moderate thermal barrier between the thermal pack and the skin of the patient.

Another object of this invention is to provide an improved absorbent pad and thermal pack which provides a substantial insulating layer between the thermal pack and the ambient for directing the thermal pack to the skin of the patient.

Another object of this invention is to provide an improved insulation for a thermal pack wherein a moderate insulating layer is interposed between the thermal pack and the skin of the patient for providing a moderate thermal barrier and a substantial insulating layer is interposed between the thermal pack and the ambient.

Another object of this invention is to provide an improved insulation for a thermal pack wherein a moderate insulating layer is interposed between the thermal pack and the skin of the patient and a substantial insulating layer is interposed between the thermal pack and the ambient for extending the useful life of the thermal pack.

The foregoing has outlined some of the more pertinent objects of the present invention. These objects should be construed as being merely illustrative of some of the more prominent features and applications of the invention. Many other beneficial results can be obtained by applying the disclosed invention in a different manner or modifying the invention with in the scope of the invention. Accordingly other objects in a full under standing of the invention may be had by referring to the summary of the invention, the detailed description describing the preferred embodiment in addition to the scope of the invention defined by the claims taken in conjunction with the accompanying drawings.

SUMMARY OF THE INVENTION

The present invention is defined by the appended claims with specific embodiments being shown in the attached drawings. For the purpose of summarizing the invention, the invention relates to a method and apparatus for an improved absorbent pad and thermal pack including an outer sheet made of a liquid impermeable material having an outer surface and an inner surface. An inner sheet made of a liquid permeable material has an outer surface and an inner surface. An absorbent sheet is disposed between the inner sheet and the outer sheet for absorbing liquid discharged from the patient. A thermal source comprising a flexible liquid impermeable container containing a chemical mixture which undergoes an thermal reaction upon activation of the chemical mixture is interposed between the outer and inner sheets enabling the thermal source to be applied to the patient and enabling any liquid from the patient to permeate through the inner sheet to be absorbed by the absorbent sheet.

In one specific embodiment of the invention, the improved absorbent pad and thermal pack includes the outer sheet being generally elongated and extending between a first end and a second end along the elongated dimension. The outer sheet is generally rounded at junctures of the first and second ends and first and second sides of the outer sheet. The outer sheet defines a first and a second recess in the first and second sides generally midpoint between the first and second ends whereby the transverse dimension midpoint of the first and second ends is less than the transverse dimension proximate the first and second ends. The inner sheet is elongated and extends between a first end and a second end. The inner sheet has a transverse dimension extending between a first and a second side. An absorbent sheet is disposed between the inner sheet and the outer sheet for absorbing liquid discharged from the patient. A thermal source comprising a flexible liquid impermeable container containing a chemical mixture which undergoes a thermal reaction upon activation of the chemical mixture is interposed between the outer and inner sheets enabling the thermal source to be applied to the patient and enabling any liquid from the patient to permeate through the inner sheet to be absorbed by the absorbent sheet.

In a more specific embodiment of the invention, the first and second ends and the first and second sides of the outer sheet define an outer sheet perimeter whereas the first and second ends and the first and second sides of the inner sheet define an inner sheet perimeter with the inner sheet perimeter approximating the outer sheet perimeter. The outer sheet is affixed to the inner sheet by adhesive means for affixing the inside surface of the inner sheet proximate the inner sheet perimeter to the inside surface of the outer sheet proximate the outer sheet perimeter.

Preferably, the absorbent sheet has a generally elongated dimension extending between a first end and a second end along the elongated dimension of the absorbent sheet and defines a transverse dimension extending between a first and a second side of the absorbent sheet. The absorbent sheet may be generally rounded at junctures of the first and second ends and the first and second sides of the absorbent sheet and may define a first and a second recess in the first and second sides generally midpoint between the first and second ends whereby the transverse dimension midpoint of the first and second ends is less than the transverse dimension proximate the first and second ends of the absorbent sheet. The first and second ends and the first and second sides of the absorbent sheet define an absorbent sheet perimeter with the absorbent sheet being smaller than the inner sheet perimeter and the outer sheet perimeter enabling the adhesive means to affix the inside surface of the inner sheet proximate the inner sheet perimeter to the inside surface of the outer sheet proximate the outer sheet perimeter with the absorbent sheet being interposed therebetween. The absorbent sheet is preferably located immediately adjacent to the inner side of the outer sheet.

The flexible liquid impermeable container of the thermal source has an elongated dimension and a transverse dimension defining a shape of a generally rectangular prism with the transverse dimension of the thermal source cooperating with the transverse dimension of the inner sheet and the outer sheet for inhibiting transverse movement of the thermal source within the absorbent pad. In one embodiment of the invention, adhesive means is secured to the outer surface of the outer sheet for removably securing the absorbent pad to an outer garment of the patient for inhibiting movement of the absorbent pad relative to the patient.

In another embodiment of the invention, the outer sheet is generally circular and generally larger in diameter than a circular inner sheet. An circular absorbent sheet is disposed between the inner sheet and the outer sheet for absorbing liquid discharged from the patient. A thermal source comprising a circular flexible liquid impermeable container containing a chemical mixture which undergoes a thermal reaction upon activation of the chemical mixture is interposed between the outer and inner sheets enabling the thermal source to be applied to the patient and enabling any liquid from the patient to permeate through the inner sheet to be absorbed by the absorbent sheet. The outer periphery of the outer sheet contains an adhesive for adhesively fastening the improved absorbent pad and thermal pack to the patient.

The invention is also incorporated into the method of making an improved absorbent pad and thermal pack for absorbing liquid discharged from a patient, comprising the steps of cutting an outer sheet from a liquid impermeable material to have a generally elongated dimension extending between a first end and a second end along the elongated dimension and with a transverse dimension extending between a first and a second side of the outer sheet. An inner sheet is cut from a liquid permeable material to have an elongated dimension extending between a first end and a second end and a transverse dimension extending between a first and a second side. The first and second ends and the first and second sides of the inner sheet is positioned adjacent the first and second ends and the first and second sides of the outer sheet, respectively, with an absorbent sheet disposed between the inner sheet and the outer sheet. The first end and the first and second sides of the inner sheet is affixed to the first end and the first and second sides of the outer sheet, respectively, to form an aperture adjacent the first ends of the inner sheet and the outer sheet. A flexible liquid impermeable container is formed containing a chemical mixture which undergoes a thermal reaction upon activation of the chemical mixture. The flexible liquid impermeable container is inserted between the inner sheet and outer sheet through the aperture adjacent the first ends of the inner sheet and the outer sheet and the second end of the inner sheet is affixed to the second end of the outer sheet to close the aperture adjacent the first ends of the inner sheet and the outer sheet to form the improved absorbent pad. The improved absorbent pad may then be positioned relative to the patient for enabling the thermal source to be applied to the patient and enabling liquid discharged from the patient to permeate through the inner sheet to be absorbed by the absorbent sheet.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which.

Similar reference characters refer to similar parts throughout the several Figures of the drawings.

DETAILED DISCUSSION

Figure 1:
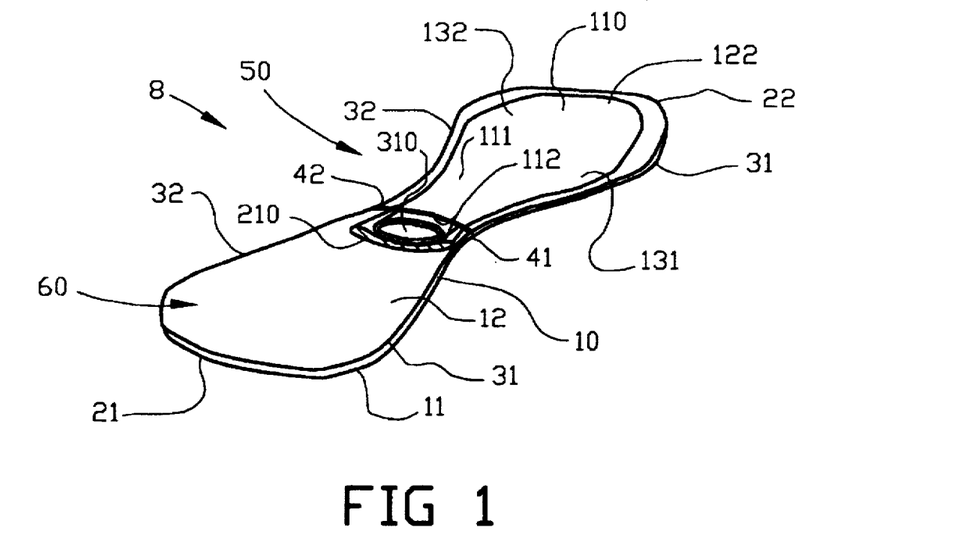
FIG. 1 is an isometric view of a first embodiment of an improved absorbent pad and thermal pack of the present invention.

FIG. 1 is an isometric view partially cut out of an improved absorbent pad 8 of the present invention comprising an outer sheet 10 having an outer surface 11 and an inner surface 12 fabricated from a generally flexible, liquid permeable material such as a thermo bonded polypropylene or the like. The outer sheet 10 has a generally elongated dimension extending between a first end 21 and a second end 22. The outer sheet 10 has a transverse dimension extending between a first side 31 and a second side 32. The outer sheet 10 is generally rounded at the junctures of the first and second ends 21 and 22 and the first and second side 31 and 32 as shown in the top and bottom views of the inventions of FIGS. 2 and 4.

Figure 2:
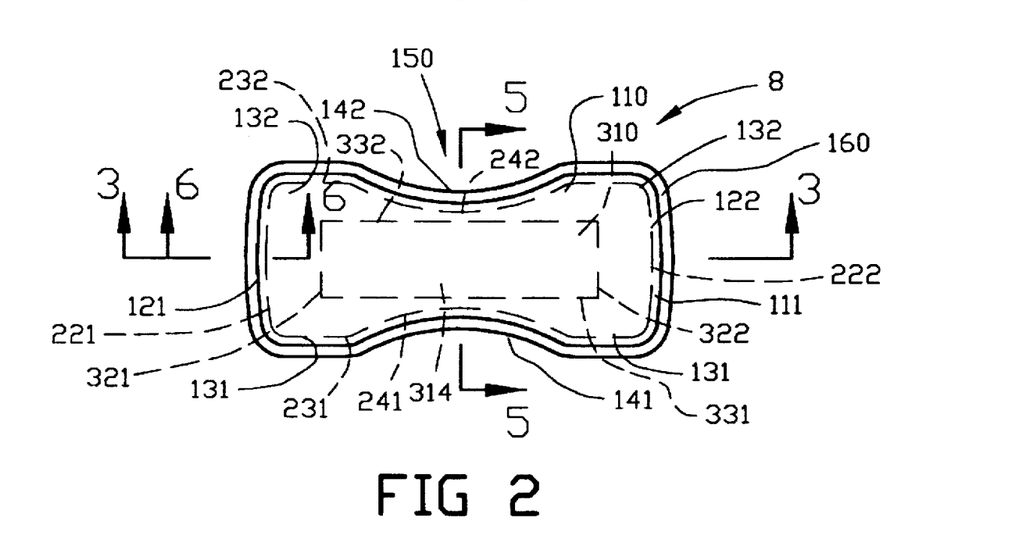
FIG. 2 is a top view of the improved absorbent pad and thermal pack shown in FIG. 1.
Figure 4:
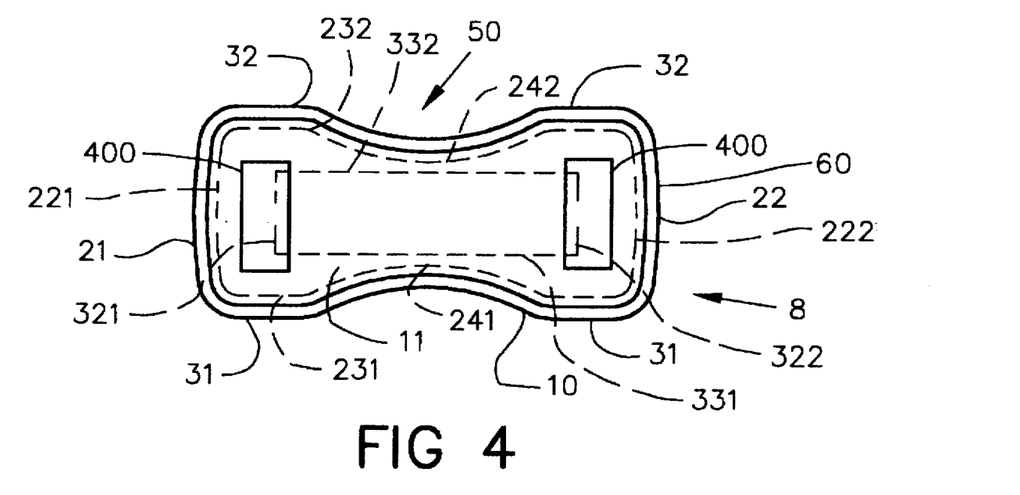
FIG. 4 is a bottom view of the improved absorbent pad and thermal pack shown in FIG. 1.

The outer sheet 10 has a first and a second recess 41 and 42 defined in the first and second sides 31 and 32 generally midpoint between the first and second ends 21 and 22. The transverse dimension at the midpoint 50 of the first and second ends 21 and 22 is less than the transverse dimension proximate the first and second ends 21 and 22.

An inner sheet 110 has an outer surface 111 and an inner surface 112 and is preferably made of a flexible liquid permeable material such as a polyester or nylon. As shown in FIG. 2, the inner sheet 110 has an elongated dimension extending between a first end 121 and a second end 122 and similarly defines a transverse dimension extending between a first and a second side 131 and 132 respectively. In a similar manner, the inner sheet 110 is generally rounded at the junctures of the first and second ends 121 and 122 and the first and second sides 131 and 132 of the inner sheet 110. The inner sheet 110 defines a first and a second recess 141 and 142 generally at a midpoint 150 between the first and second ends 121 and 122. The transverse dimension at the midpoint 150 of the first and second ends 121 and 122 is less than the transverse dimension proximate the first and second ends 121 and 122.

Figure 3:
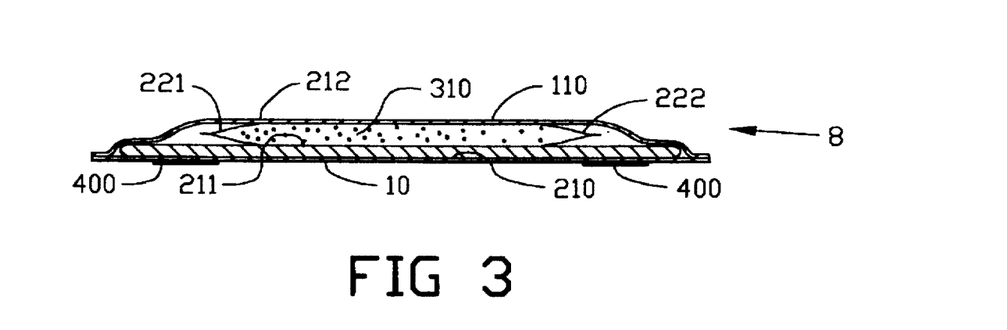
FIG. 3 is a sectional view along line 3—3 of FIG. 2.

An absorbent sheet 210 shown in phantom in FIGS. 2 and 4 and shown in section in FIG. 3 is made of a liquid absorbent material and has an outer surface 211 and an inner surface 212. The absorbent pad 210 extends between a first and a second end 221 and 222 which is slightly less than the elongated dimension of the outer sheet 10 and the inner sheet 110. The absorbent material 210 defines a transverse dimension extending between a first side 231 and a second side 232.

Figure 5:
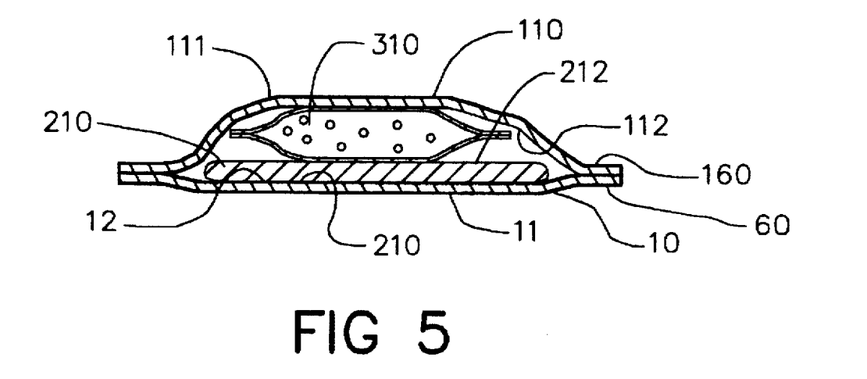
FIG. 5 is a sectional view along line 5—5 of FIG. 2.

The absorbent sheet 210 has a first and a second recess 241 and 242 defined in the first and second sides 231 and 232 generally midpoint between the first and second ends 221 and 222. The transverse dimension at a midpoint of the first and second ends 221 and 222 is less than the transverse dimension proximate the first and second ends 221 and 222. The outer surface 211 of the absorbent material 210 is disposed adjacent the inner surface of the outer sheet 10 as shown in FIGS. 1, 3 and 5. The transverse dimension of the absorbent pad 210 extending between the first and the second end 221 and 222 is slightly less than the transverse dimension of the outer sheet 10 and the inner sheet 110 thereby defining an outer sheet perimeters 60 of the outer sheet 10 and defining an inner sheet perimeters 160 of the inner sheet 110 as shown in FIGS. 2 and 4.

Figure 7:
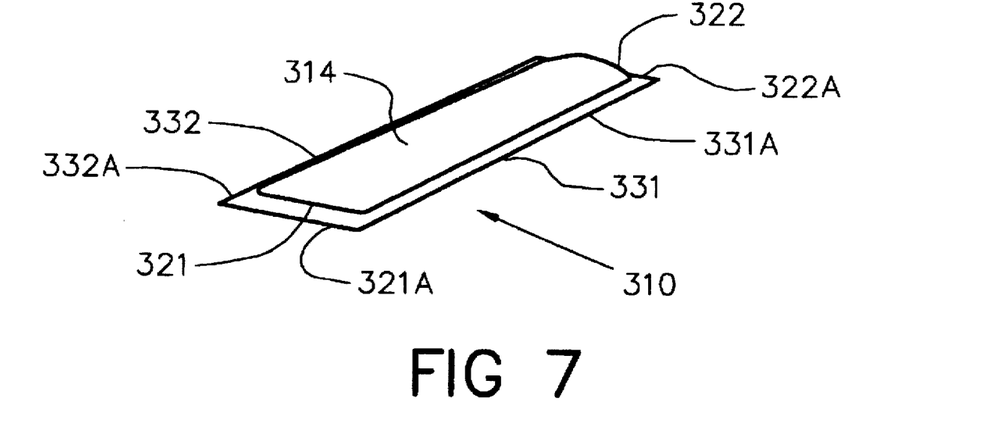
FIG. 7 is an enlarged isometric view of the thermal pack removed from the improved absorbent pad and thermal pack of FIGS. 1–6.
Figure 8:
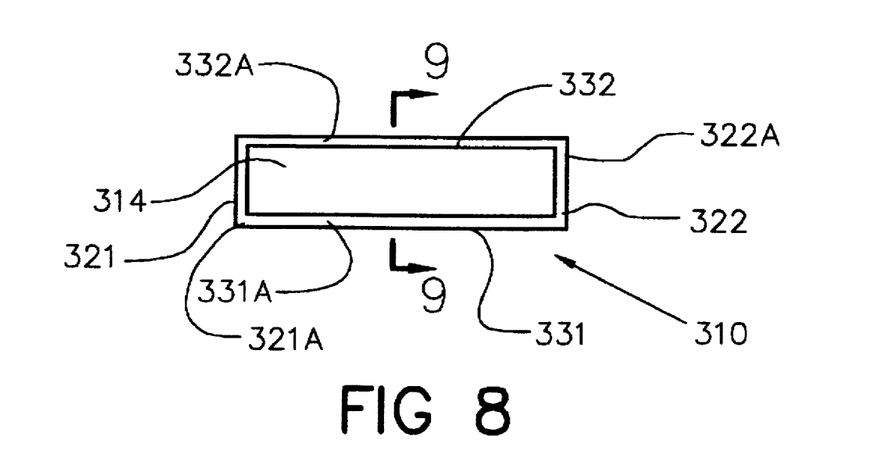
FIG. 8 is a top view of the thermal pack shown in FIG. 7.
Figure 9:
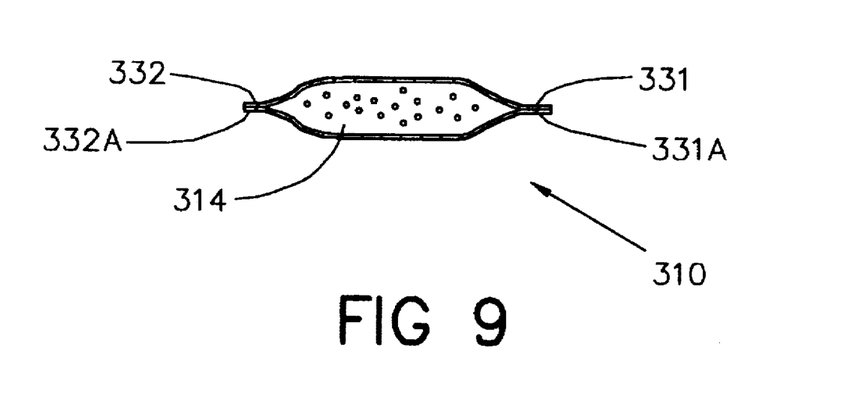
FIG. 9 is a sectional view along line 9—9 of FIG. 8.

A thermal source 310 shown more specifically in FIGS. 7–9 comprises a flexible, liquid impermeable container 314 extending from a first end 321 to a second end 322 defining a generally elongated dimension of the flexible container 314. The flexible container 314 also defines a transverse dimension between a first and a second side 331 and 332. As best shown in FIGS. 7 and 9, the flexible container 314 may be formed by heat sealing two sheets of a flexible plastic material in seams 321A on the first end 321, a seam 322A on the second end 322 seam 331A on the first side 331 and a seam 332A on the second side 332 for entrapping a chemical mixture 340 therein. The chemical mixture 340 contained within the flexible container 314 is a mixture which undergoes a thermal reaction upon the mixing of the two chemicals substances. The thermal reaction produced upon the mixing of the two chemicals substances either may be an endothermic reaction (heat absorbing) or may be an exothermic reaction (heat producing). Substances that are suitable for use in the flexible container for cold pack or an endothermic reaction are sodium nitrate and water as shown be well known to those skilled in the art. Substances that are suitable for use in the flexible container for heat pack or an exothermic reaction are magnesium sulfate anhydrous, colloidal clay and water as shown be well known to those skilled in the art. It should be also appreciated that various other chemical formulations may be used within the flexible container 314 of the present invention.

The thermal pack 310 forms a generally rectangular prism with a substantially constant transverse dimension between the first and second sides 331 and 332. The transverse dimension of the flexible container 314 is generally commensurate with the transverse dimension of the outer and inner sheets 10 and 110 proximate the midpoints 50 and 150. As best shown in FIGS. 1, 3 and 5, the thermal pack 310 is disposed within the improved absorbent pad 8 immediately adjacent the inner sheet 110.

The improved absorbent pad and cold pack 8 of the present invention is assembled in the relationship shown in FIGS. 1–6. The outer surface 211 of the absorbent pad 210 is preferably affixed to the inner surface 12 of the outer sheet 10 by suitable means such as heat sealing, gluing and the like for maintaining the position of the absorbent material 210 relative to the outer sheet 10. The thermal pack 310 is interposed between the inner surface 212 of the absorbent pad and the inner surface 112 of the inner sheet 110 as best shown in FIGS. 1, 3 and 5. The outer sheet perimeter 60 of the outer sheet 10 is sealed to the inner sheet perimeter 160 of the inner sheet 110.

Figure 6:
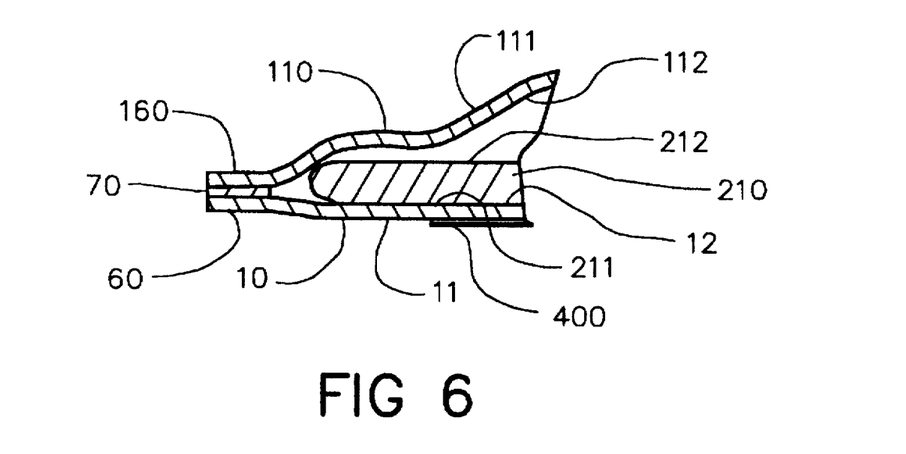
FIG. 6 is an enlarged view along line 6—6 of a portion of the improved absorbent pad and thermal pack shown in FIG. 2.

As best shown in FIGS. 6, the perimeters 60 and 160 are preferably adhesively affixed to one another by the introduction of an interposed adhesive 70 between the inner surface 12 of the outer sheet 10 and the inner surface 112 of the inner sheet 110. Since the absorbent material 210 is smaller than the inner and outer sheets 10 and 110, the absorbent material 210 does not form apart of the affixing of the outer sheet 10 to the inner sheet 110.

Since the elongated longitudinal dimension between the first and second ends 321 and 322 of the flexible container 314 is smaller than the elongated dimension between the first and second ends 21 and 22 of the outer sheet 10 and the first and second ends 121 and 122 of the inner sheet 110, the thermal pack 210 will migrate to the proper position when the absorbent pad 8 is worn by a user in the event that the improved absorbent pad 8 is not properly positioned by the user. Furthermore, more, since the transverse dimension of the container 314 is generally commensurate with the transverse dimension at the midpoints 50 and 150 of the outer sheet 10 and the inner sheet 110, the flexible container 314 is restricted from lateral movement within the improved absorbent pad 8.

Adhesive means 400 may be optionally included on the outer surface 11 of the outer sheet 10 for removably affixing the improved absorbent pad 8 to an inside surface of an undergarment of the user.

The invention is also incorporated into the method of making the improved absorbent pad 8 for absorbing liquid discharged from a patient, comprising the steps of cutting the outer sheet 10 from a liquid impermeable material to have a generally elongated dimension extending between the first end 21 and the second end 22 along the elongated dimension and with a transverse dimension extending between the first side 31 and the second side 32 of the outer sheet 10. The inner sheet 110 is cut from a liquid permeable material to have an elongated dimension extending between a first end 121 and a second end 122 and a transverse dimension extending between the first side 131 and the second side 132. The first and second ends 21 and 22 and the first and second sides 31 and 32 of the inner sheet 10 is positioned adjacent the first and second ends 121 and 122 and the first and second sides 131 and 132 of the outer sheet 110, respectively, with the absorbent sheet 310 disposed between the inner sheet 110 and the outer sheet 10. The first end 121 and the first and second sides 131 and 132 of the inner sheet 110 is affixed to the first end 21 and the first and second sides 31 and 32 of the outer sheet 10, respectively, to form an aperture (not shown) adjacent the second end 132 of the inner sheet 110 and the second end 32 of the outer sheet 10. The flexible liquid impermeable container 314 contains a chemical mixture which undergoes an endothermic reaction upon activation of the chemical mixture. The flexible liquid impermeable container 314 is inserted between the inner sheet 110 and outer sheet 10 through the aperture adjacent the second end 132 of the inner sheet 110 and the second end 32 of the outer sheet 10. The second end 132 of the inner sheet 110 is affixed to the second end 32 of the outer sheet 10 to close the aperture (not shown) adjacent the second end 132 of the inner sheet 110 and the second end 32 of the outer sheet 10 to form the improved absorbent pad 8.

Preferably, the outer sheet 10 is cut to define the first and second recesses 41 and 42 in the first and second sides 31 and 32 at the midpoint 50 between the first and second ends 21 and 22. In a similar manner, the inner sheet 110 is cut to define the first and the second recess 141 and 142 in the first and second sides 131 and 132 at the midpoint 150 between the first and second ends 121 and 122. The first end 121 and the first and second sides 131 and 132 of the inner sheet 110 is preferably glued to the first end 21 and the first and second sides 31 and 32 of the outer sheet 10. Similarly, the second end 122 of the inner sheet 110 is glued to the second end 22 of the outer sheet 10 after the flexible liquid impermeable container 314 is inserted between the inner sheet 110 and outer sheet 10 through the aperture. An adhesive 400 may be secured to the outer surface 11 of the outer sheet 10 for removably securing the absorbent pad 8 to an outer garment of the patient for inhibiting movement of the absorbent pad relative to the patient.

Figure 10:
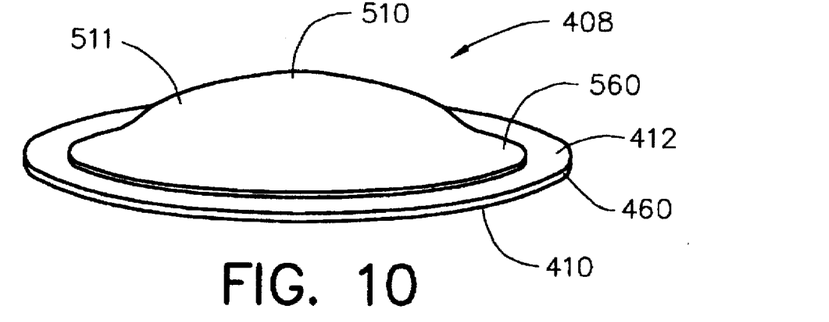
FIG. 10 is an isometric view of a second embodiment of an improved absorbent pad and thermal pack of the present invention.
Figure 11:
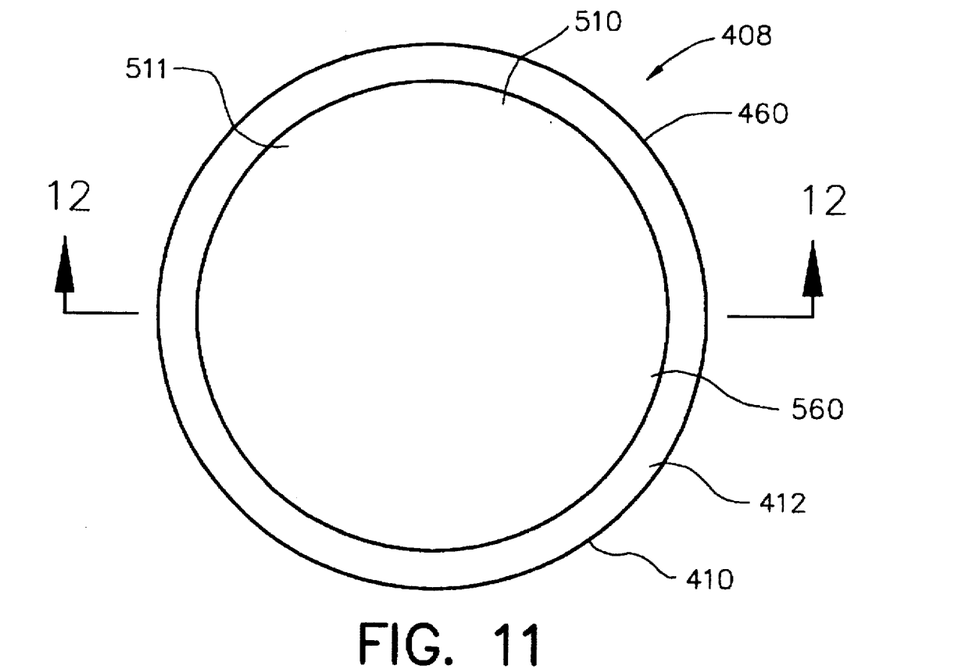
FIG. 11 is a bottom view of the improved absorbent pad and thermal pack shown in FIG. 10.
Figure 12:
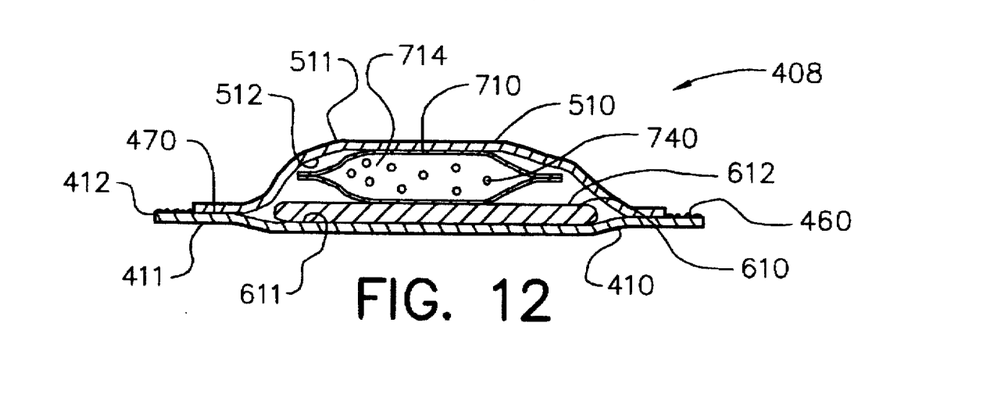
FIG. 12 is a sectional view of the improved absorbent pad and thermal pack shown in FIG. 10.

FIGS. 10–12 illustrate a second embodiment of the improved absorbent pad and thermal pack 408 of the present invention comprising an outer sheet 410 having an outer surface 411 and an inner surface 412 fabricated from a generally flexible, liquid permeable material. The outer sheet 410 is generally circular having an outer sheet perimeter 460. An inner sheet 510 has an outer surface 511 and an inner surface 512 and is preferably made of a flexible liquid permeable material such as a polyester or nylon. The inner sheet 510 is generally circular having an inner sheet perimeter 560 which is less than the outer sheet perimeter 460 of the outer sheet 410.

An absorbent sheet 610 is made of a liquid absorbent material and has an outer surface 611 and an inner surface 612. The absorbent pad 610 is circular and has a perimeter which is slightly less than the inner sheet perimeter 560 of the inner sheet 510. The outer surface 611 of the absorbent material 610 is disposed adjacent the inner surface 412 of the outer sheet 410 as shown in FIG. 12.

A thermal source 710 comprising a flexible, liquid impermeable container 714 is generally circular and commensurate in perimeter to the perimeter of the absorbent pad 610. The flexible container 714 may be formed by heat sealing two sheets of a flexible plastic material in seams as heretofore described for entrapping a chemical mixture 740 therein. The chemical mixture 740 undergoes a thermal reaction upon the mixing of the chemicals substances.

The outer surface 611 of the absorbent pad 610 is affixed to the inner surface 412 of the outer sheet 410 by suitable means such as heat sealing, gluing and the like. The thermal peck 710 is interposed between the inner surface 612 of the absorbent pad 610 and the inner surface 512 of the inner sheet 510. The outer sheet 410 is sealed to the inner sheet 510 by means such as adhesive means 470 or the like.

Adhesive means 800 is disposed on the inner surface 411 of outer sheet perimeter 460 of the outer sheet for affixing the improved absorbent pad 408 to the user. The adhesive means 800 allows the improved absorbent pad and thermal peck 408 to be used on and affixed to substantially any skin portion of a patent with the use of additional garments or other support devices.

The inner sheet of the present invention provides a moderate insulating layer interposed between the thermal pack and the skin of the patient. The moderate thermal barrier between the thermal pack and the skin of the patient eliminates the direct contact of the thermal pack with the skin of the patient. The absorbent pad provides a substantial insulating layer between the thermal pack and the ambient, that is, away from the skin of the patient.

The combination of the moderate insulating layer of the inner sheet and the substantial insulating layer of the absorbent pad provides several unique and unexpected benefits over the prior art. First, the moderate insulating layer of the inner sheet makes the application of either cold or hot more comfortable for the patient since there is no direct contact of the thermal pack with the skin of the patient. Second, the moderate insulating layer of the inner sheet directs the cold or heat from the thermal pack toward the skin of the patient at a rate slower than a conventional cold pack. Third, the substantial insulating layer of the absorbent pad inhibits the flow of cold or heat between the thermal pack and the ambient. Fourth, the combination of the moderate insulating layer of the inner sheet and the substantial insulating layer of the absorbent pad extends the useful life of the thermal pack by the inner sheet retarding the flow of cold or heat between the thermal pack and the skin of the patient and by the absorbent pad inhibiting the flow of cold or heat between the thermal pack and the ambient.

The improved absorbent pad of the present invention has found to be effective during the recovery of post-natal operations as well as other gynecological operations. The improved pad and thermal pack provides both an absorbent media for absorbing a liquid discharged from a patient as well as providing cooling or heating for a treated area by virtue of the combined thermal pack within the improved absorbent pad. Since the inner sheet provides a moderate amount of insulation value, the thermal surface of the flexible plastic container is not directly applied to the skin of the patient, thus making the device more suitable for use than the prior art devices. Furthermore, the substantial insulation valve of the absorbent pad enhances the effectiveness of the thermal pack.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. An improved absorbent pad and thermal pack for absorbing a liquid discharged from a patient, comprising in combination:

an outer sheet portion and an inner sheet portion;

said outer sheet portion having an outer surface and an inner surface;

said inner sheet portion having an outer surface and an inner surface with said inner sheet portion being made of a liquid permeable material;

said inner sheet portion providing a moderate thermal barrier;

an absorbent sheet having an inner surface and an outer surface;

said absorbent sheet being greater in thickness than said inner sheet portion for providing a substantial thermal barrier which is substantially greater than the moderate thermal barrier of said inner sheet portion;

a thermal pack comprising a flexible liquid impermeable container containing a chemical mixture which undergoes a thermal reaction upon activation of the chemical mixture;

said outer sheet portion being connected to said inner sheet portion for enclosing said thermal pack and said absorbent sheet with said thermal pack being interposed between said absorbent sheet and said inner sheet portion and being in direct contact with said inner surface of said inner sheet portion enabling said thermal pack to cool said patient and with said liquid permeable material of said inner sheet portion enabling any liquid from the patient to permeate through said inner sheet portion to be absorbed by said absorbent sheet;

said absorbent sheet establishing a substantial thermal insulator between said thermal pack and a temperature of ambient air and with said inner sheet portion establishing a moderate thermal insulator between said thermal pack and the patient for providing a preferential flow of heat between the patient and said thermal pack relative to the flow of heat between the ambient air and the thermal pack; and said inner sheet portion being substantially thinner than said absorbent sheet for allowing the liquid discharged from the patient to migrate through said inner sheet portion to said absorbent sheet wherein the majority of the liquid discharged from the patient is absorbed by said absorbent sheet.

2. An improved absorbent pad and thermal pack as set forth in claim 1, including adhesive means for securing the improved absorbent pad and thermal pack to a patient.

3. An improved absorbent pad and thermal pack as set forth in claim 1, including adhesive means secured to said outer surface of said outer sheet portion for removably securing said absorbent pad to an outer garment of said patient for inhibiting movement of said absorbent pad relative to said patient.

4. An improved absorbent pad and thermal pack as set forth in claim 1, wherein said inner sheet portion and said outer sheet portion are substantially elongated.

5. An improved absorbent pad and thermal pack as set forth in claim 1, wherein said absorbent sheet being enclosed between said inner sheet portion and said outer sheet portion includes said absorbent sheet being disposed immediately adjacent to said inner side of said outer sheet portion.

6. An improved absorbent pad and thermal pack as set forth in claim 1, wherein said thermal pack comprises said flexible liquid impermeable container.

7. An improved absorbent pad and thermal pack as set forth in claim 1, including adhesive means for affixing a first and a second end of said inner sheet portion to a first and a second end of said outer sheet portion.

8. An improved absorbent pad and thermal pack for absorbing a liquid discharged from a patient, comprising in combination:

an outer sheet portion and an inner sheet portion;

said outer sheet portion having an outer surface and an inner surface;

said inner sheet portion having an outer surface and an inner surface with said inner sheet portion being made of a liquid permeable material;

said inner sheet portion providing a moderate thermal barrier;

an absorbent sheet having an inner surface and an outer surface;

said absorbent sheet being greater in thickness than said inner sheet portion for providing a substantial thermal barrier which is substantially greater than the moderate thermal barrier of said inner sheet portion;

a thermal pack comprising a flexible liquid impermeable container containing a chemical mixture which undergoes a thermal reaction upon activation of the chemical mixture;

said outer sheet portion being connected to said inner sheet portion for enclosing said thermal pack and said absorbent sheet with said thermal pack being interposed between said absorbent sheet and said inner sheet portion and being immediately adjacent with said inner surface of said inner sheet portion enabling said thermal pack to cool said patient and with said liquid permeable material of said inner sheet portion enabling any liquid from the patient to permeate through said inner sheet portion to be absorbed by said absorbent sheet;

said absorbent sheet establishing a substantial thermal insulator between said thermal pack and a temperature of ambient air and with said inner sheet portion establishing a moderate thermal insulator between said thermal pack and the patient for providing a preferential flow of heat between the patient and said thermal pack relative to the flow of heat between the ambient air and the thermal pack; and said inner sheet portion being substantially thinner than said absorbent sheet for allowing the liquid discharged from the patient to migrate through said inner sheet portion to said absorbent sheet wherein the majority of the liquid discharged from the patient is absorbed by said absorbent sheet.

9. An improved absorbent pad and thermal pack as set forth in claim 8, including adhesive means for securing the improved absorbent pad and thermal pack to a patient.

10. An improved absorbent pad and thermal pack as set forth in claim 8, including adhesive means secured to said outer surface of said outer sheet portion for removably securing said absorbent pad to an outer garment of said patient for inhibiting movement of said absorbent pad relative to said patient.

11. An improved absorbent pad and thermal pack as set forth in claim 8, wherein said inner sheet portion and said outer sheet portion are substantially elongated.

12. An improved absorbent pad and thermal pack as set forth in claim 8, wherein said absorbent sheet being enclosed between said inner sheet portion and said outer sheet portion includes said absorbent sheet being disposed immediately adjacent to said inner side of said outer sheet portion.

13. An improved absorbent pad and thermal pack as set forth in claim 8, wherein said thermal pack comprises said flexible liquid impermeable container.

14. An improved absorbent pad and thermal pack as set forth in claim 8, including adhesive means for affixing a first and a second end of said inner sheet portion to a first and a second end of said outer sheet portion.

15. An improved absorbent pad and thermal pack for absorbing a liquid discharged from a patient, comprising in combination:

an outer sheet portion and an inner sheet portion;

said outer sheet portion having an outer surface and an inner surface;

said inner sheet portion having an outer surface and an inner surface with said inner sheet portion being made of a liquid permeable material;

said inner sheet portion providing a moderate thermal barrier;

an absorbent sheet having an inner surface and an outer surface;

said absorbent sheet being greater in thickness than said inner sheet portion for providing a substantial thermal barrier which is substantially greater than the moderate thermal barrier of said inner sheet portion;

a thermal pack comprising a flexible liquid impermeable container containing a chemical mixture which undergoes a thermal reaction upon activation of the chemical mixture;

said outer sheet portion being connected to said inner sheet portion for enclosing said thermal pack and said absorbent sheet with said thermal pack being interposed between said absorbent sheet and said inner sheet portion;

said inner sheet portion enabling said thermal pack to cool said patient and with said liquid permeable material of said inner sheet portion enabling any liquid from the patient to permeate through said inner sheet portion to be absorbed by said absorbent sheet;

said absorbent sheet establishing a substantial thermal insulator between said thermal pack and a temperature of ambient air and with said inner sheet portion establishing a moderate thermal insulator between said thermal pack and the patient for providing a preferential flow of heat between the patient and said thermal pack relative to the flow of heat between the ambient air and the thermal pack; and said inner sheet portion being substantially thinner than said absorbent sheet and being the sole sheet interposed between said thermal pack and the patient for allowing the liquid discharged from the patient to migrate through said inner sheet portion to said absorbent sheet wherein the majority of the liquid discharged from the patient is absorbed by said absorbent sheet.

* * * * *